United States Patent [19]

Baxendale et al.

[11] Patent Number: 5,464,621
[45] Date of Patent: Nov. 7, 1995

[54] CANINE CORONA VIRUS VACCINE

[75] Inventors: William Baxendale, Huntingdon; William S. K. Chalmers, St. Ives, both of United Kingdom

[73] Assignee: Akzo N.V., Arnhem, Netherlands

[21] Appl. No.: 285,611

[22] Filed: Aug. 3, 1994

Related U.S. Application Data

[60] Continuation of Ser. No. 70,079, Jun. 1, 1993, abandoned, which is a division of Ser. No. 514,069, Apr. 25, 1990, Pat. No. 5,232,694.

[30] Foreign Application Priority Data

May 3, 1989 [EP] European Pat. Off. .............. 89304441

[51] Int. Cl.$^6$ ............................ A61K 39/215; C12N 7/08
[52] U.S. Cl. .................... 424/221.1; 424/818; 435/237; 435/948
[58] Field of Search .................... 424/221.1, 818; 435/948, 237

[56] References Cited

U.S. PATENT DOCUMENTS

| 4,567,042 | 1/1986 | Acree et al. . |
| 4,567,043 | 1/1986 | Acree et al. . |
| 4,824,785 | 4/1989 | Acree et al. . |

FOREIGN PATENT DOCUMENTS

| 0138242 | 4/1985 | European Pat. Off. . |
| 0295057 | 12/1988 | European Pat. Off. . |
| WO88/01292 | 2/1988 | WIPO . |

OTHER PUBLICATIONS

Appel M, "Canine Coronovirus" in *Virus Infections of Carnivores,* Appel M. J. ed, Chapter–11, Elsevier Science (Amsterdam) 1987, pp. 115–122.

Boslego et al, "Gonorrhea Vaccines" in Vaccines and Immunotherapy, Cryz S. J. ed, Chapter 17, Pergamon Press (New York), 1991 pp. 211–223.

Kallings et al "Placebo Controlled trial of two acellular pertussis Vaccines in Sweden–Protective efficacy and adverse events." Lancet I: 956–960, 1988.

*Primary Examiner*—Christine M. Nucker
*Assistant Examiner*—Julie Krsek-Staples
*Attorney, Agent, or Firm*—William M. Blackstone; Mary E. Gormley

[57] ABSTRACT

A live or inactivated canine corona virus vaccine is provided which is derived from a virus of the novel antigenic type of the canine corona virus strain I-743 (CNCM, Institut Pasteur, Paris). A method for the preparation of this vaccine and the use of said vaccine in protecting susceptible animals against canine corona virus injection are also disclosed.

1 Claim, No Drawings

CANINE CORONA VIRUS VACCINE

This is a continuation of application Ser. No. 08/070,079 filed Jun. 1, 1993, now abandoned, which is a division of U.S. Ser. No. 07/514,069, filed Apr. 25, 1990, now U.S. Pat. No. 5,232,694.

The present invention is concerned with a vaccine for the protection of susceptible animals against canine coronavirus infections, canine corona viruses of a novel antigenic type and their use in the preparation of such a vaccine, as well as the application of this vaccine in the protection of susceptible animals against canine corona virus infection.

The corona viruses are classified as a distinct viral genus. Viruses belonging to this genus are known to infect a variety of animal species including man. They cause diverse diseases, such as gastroenteritis (in swine, turkeys, mice, calves, dogs, cats and man), salivary gland infection (in rodents), respiratory disease (in man, swine, avians and dogs) and encephalitis (in young swine).

Within the genus of Corona viruses a group of viruses can be discerned which forms a distinct antigenic cluster. The feline infectious peritonitis virus (FIPV) and the feline enteritis virus (FEV) of cat, the transmissible gastroenteritis virus (TGEV) and the porcine corona virus (PCV) of pigs, the canine corona virus of dogs (CCV) and the virus CV229E of man all belong to this group. Members of this antigenic cluster do not cross-react with other corona viruses such as mouse hepatitis virus type 3, calf diarrhoea virus, haemagglutinating encephalomyelitis virus of swine, human corona virus OC 43 and the avian infectious bronchitis virus.

CCV was first isolated from military dogs in Germany in 1971. The signs following infection include vomiting, diarrhoea, anorexia, depression and dehydration. Mortality may occur under certain circumstances (stress). Respiratory disease has been reported including nasal and ocular discharge. The incidence of antibody in different countries varies. In the UK up to 40% of household dogs have antibodies against CCV whereas kennel dogs have a higher incidence.

Although CCV inoculation of cats and pigs results in infection no clinical disease will be caused by CCV in these species. The agent can be isolated from the oropharynx and faeces, and there is an antibody response. There is no evidence that humans, cattle and mice are susceptible to CCV.

Cross protection studies have shown that the Corona viruses induce little (or no) immunity to each other. For example experimental infection of dogs with TGEV or FIPV does not protect them against the effects of a subsequent CCV infection.

Various vaccines have been developed against CCV. An inactivated vaccine containing adjuvant has been used in the USA. A live attenuated vaccine protected animals against the CCV strain known at the time but as it was shown to be incompatible with multivalent vaccines, it has been withdraw from the market.

Surprisingly it has been found now that a new strain of CCV could be isolated from dogs with CCV disease. This new virus was assigned the internal notation IN/SAV/Cl and was deposited with the Collection Nationale de Cultures de Micro-organismes of Institut Pasteur at 28, rue du Dr Roux, 75724 Paris Cedex 15, France having the accession number I-743 A characteristic property of this virus is that it is not neutralized to any great extent in a neutralization test with antisera to the known isolates of CCV. However, antisera against IN/SAV/Cl neutralizes to high titres all known American strains as well as the IN/SAV/Cl strain itself. Henceforth, it can be concluded that this novel strain of CCV represents a hitherto unknown antigenic type of CCV; up till now significant antigenic variation had not been reported for CCV.

In view of this discovery, according to the present invention a novel vaccine is provided which upon administration to susceptible animals protects these animals against the clinical effects of CCV infection. This novel vaccine is derived from a virus strain of the antigenic type of the novel CCV strain having the internal notation IN/SAV/Cl.

This novel vaccine can be administered not only to dogs but also to other animals which are susceptible to CCV infection such as cats and pigs.

Vaccines according to the invention comprise the virus either in live, optionally attenuated, or inactivated form.

Attenuation is established by serial passages of the viruses in a culture of cells, preferably originating from a canine or feline species. For each step the viruses harvested from the previous culture step are inoculated to a medium containing a fresh cell culture. For the culturing of the cells use may be made of methods known in the art.

For the preparation of the live vaccine the seed virus optionally attenuated as indicated above can be grown on a cell culture, such as a feline embryo fibro-blast (FEF) culture. The viruses thus grown can be harvested by collecting the-tissue cell culture fluids and/or cells. Optionally, during the harvesting the yield of the viruses can be promoted by techniques which improve the liberation of the infective particles from the growth substrate, e.g. sonication. The live vaccine may be prepared in the form of a suspension or may be lyophilized. In lyophilized CCV vaccines it is preferable to add one or more stabilizers. Suitable stabilizers are for example SPGA (described by Bovarnick (1950) J. Bacteriology 59, 509), carbohydrates (such as sorbitol, mannitol, starch, sucrose, dextran, glucose), proteins (such as albumin or casein) or degradation products thereof, protein containing agents (such as bovine serum or skimmed milk) and buffers (such as alkali metal phosphates). Optionally, one or more compounds having adjuvant activity may be added too. Suitable adjuvants are for example aluminium hydroxide, phosphate or oxide, mineral oils (such as Bayol F$^{(R)}$, Marcol 52$^{(R)}$) and saponins.

Live viruses preferably may be administered to the animals to be protected from an age of about 4 weeks, and more in particular at an age of between 5 and 12 weeks. In certain cases it may be recommendable to vaccinate twice, at 6 weeks and at 10 weeks for example.

The live vaccines preferably contain the virus in an amount of between $10^2$ and $10^9$ pfu/dose.

Vaccines according to the invention alternatively may comprise the CCV strain in inactivated form.

Inactivated CCV vaccines according to the invention are prepared from viruses from which both replication and virulence have been abolished. In general this can be attained by chemical or by physical means. Chemical inactivation can be carried out by treatment of the viruses for example with enzymes, with formaldehyde, β-propiolacton or ethyleneimine or a derivative thereof, with an organic solvent (such as a halogenated hydrocarbon) and/or with a detergent (such as Tween$^{(R)}$, Triton X$^{(R)}$, sodiumdesoxycholate, sulfobetain or cetyltrimethylammonium salts). Physical inactivation advantageously can be carried out by subjecting the viruses to energy-rich radiation, such as UV light, gamma-radiations or X-rays. If necessary the inactivating agent is neutralized; for example formaldehyde-inactivated preparations can be neutralized with thiosulphate. If required, the pH subsequently is returned to a value of about 7. Generally, also an adjuvant is added to the inactivated viruses, and optionally one or more emulsifiers, such as Tween(R) and Span(R).

The inactivated vaccine may preferably contain the equivalent of at least $10^7$ pfu/ml of the virus as determined prior to inactivation.

Preferably, the inactivated vaccine is administered to the animals from an age of about 4 weeks, and more in particular at an age of between 5 and 12 weeks. Where the animals are vaccinated twice, the two vaccinations preferably are separated about 4 to 6 weeks.

The vaccines according to the invention also may be combined with other vaccines. Suitably it may be administered together with one or more of the following vaccines against canine parvo virus, canine adeno virus 1 and 2, rabies virus, Leptospira and Bordetella bronchiseptica.

Isolation of Corona Virus IN/SAV/Cl

The corona virus isolate IN/SAV/Cl originated from a faeces sample from a puppy with severe gastroenteritis. The pup was from a large Beagle breeding colony with an outbreak of gastroenteritis where Parvo was suspected. Corona virus was isolated in the absence of parvovirus.

Method of Isolation

The faeces sample was diluted 1:10 in PBS with Penicillin and Streptomycin incorporated on a weight by volume ratio. The diluted sample was thoroughly mixed before filtering through a Millipore 0.22 μ filter. 0.2 ml of the faecal supernatant was adsorbed onto the cell sheet of a confluent A72 cell culture on a petri dish for 1 hour at 37° C. The petri dish was then refed with 5 ml of maintenance medium. The supernatant was harvested after six days and aliquoted into 0.5 ml amounts. (The cells were subbed at a ratio of 1:4 to see if Parvovirus could be isolated, as Parvovirus was suspected. Later this supernatant was hemagolutination ("HA") tested for Parvovirus and found to be negative). The supernatant was assayed on confluent A72 cell cultures on petri dishes, 0.2 ml per plate, two plates per dilution; absorbed for 1 hour at 37° C. and then overlayed with 6.5 ml of agar/overlay per plate. Plaques appeared which resembled corona virus plaques, and a plaque from the $10^{-3}$ dilution—(the highest dilution at which plaques appeared), was harvested. This material was adsorbed onto a confluent A72 petri dish for 1 hour at 37° C. and refed with 5 ml of maintenance medium. After 4 days a full cytapathogenic effect ("CPE") had taken effect and once again the supernatant was harvested. The material was further passaged on A72 cells in plastic 175 $cm^2$ roux sized bottles.

NB (1) Third passage seed is the virus used in the neutralisation tests.

(2) The supernatant in all cases was negative for parvovirus.

(3) The CPE resembled the CPE of other corona viruses.

(4) Fluorescent microscopy and electron microscopy also proved the isolate to be corona virus.

(5) Cross serum neutralisation tests against both positive and negative serum to other corona virus strains were carried out by means of plaque reduction.

Neutralisation Test Method

Confluent 48 hour A72 cells on petri dishes were used to carry out the serum neutralisation tests. Dilutions of the serum samples were made in PBS, to give final dilutions of 1/16, 1/64, 1/256 and 1/1024. The virus dilution was according to previous assay results. Equal amounts of virus was added to each of the serum dilutions. The serum/virus was then incubated at 37° C. for 1 hour. A Virus Control (VC) consisting of the dilution of virus used in the test was treated similarly. The medium was tipped off the petri dishes and 0.1 ml of the serum/virus dilutions was put onto each plate, using an Eppendorf pipette, two plates per dilution, plus two plates for VC, VC $10^{-1}$ and cell control without virus. The plates were adsorbed for 30 minutes in an ungassed incubator. Each plate was then overlayed with 6.5 ml of Agar/Overlay.

Plates were kept in a 5% $CO_2$ gassed 37° C., water jacketed incubator. Plaques were apparent four days post infection. Agar was flipped off the plates and 2.5 mls of Napthalene black stain was added, left for 5–10 minutes before washing off with tap water. Plaques were then easily readable. Neutralisation was said to have occurred at the dilution of serum where the plaque count was reduced by 90% as compared with the virus control.

Antisera

Antisera to the different viruses (except TGE) was prepared in cats. They were injected by the oral-nasal route and bled at intervals following infection. Sera that showed neutralising activity was used in the cross neutralisation test.

TGE antisera was prepared by infecting young pigs by the oro-nasal route. These pigs were bled subsequently.

| ANTISERUM TO VIRUS: ISOLATE: | USDA | LIVERPOOL ISOLATE | IN/SAV/Cl | POOL 189 | FIP | TGE |
|---|---|---|---|---|---|---|
| USDA | 1/2048* | 1/128 | 1/128 | 1/256 | >1/200 | 1/256 |
| LIVERPOOL ISOLATE | 1/128 | 1/128 | 1/32 | 1/64 | 1/40 | 1/256 |
| IN/SAV/Cl | <1/8 | <1/16 | 1/128 | <1/16 | 1/20 | 1/16 |
| CCV-3 | 1/256 | 1/64 | 1/64 | 1/128 | 1/200 | 1/256 |
| CCV-4 | 1/512 | 1/128 | 1/128 | 1/128 | 1/200 | 1/128 |
| POOL 189 | 1/512 | 1/128 | 1/128 | 1/256 | >1/400 | >1/256 |
| FIP | 1/16 | 1/32 | 1/64 | 1/32 | >1/200 | 1/128 |

*Represents the dilution of serum that neutralises 90% of the plaques.

EXAMPLE 1

Live canine corona virus vaccine-A

Live attenuated virus of the strain IN/SAV/Cl in a tissue culture fluid from feline embryo fibroblasts is mixed with a freeze-drying stabiliser containing per liter:

| | |
|---|---|
| 74.35 | g sucrose |
| 0.52 | g $KH_2PO_4$ |
| 2.58 | g $Na_2HPO_4 \cdot 12H_2O$ |
| 0.910 | g mono sodium glutamate |
| 30 | ml of a 30% (w/v) solution of bovine serum albumin. |

The mixture is freeze dried in vials containing about 1 ml doses of about $10^4$ pfu of the virus, and the vials are sealed.

Prior to use this freeze-dried product is reconstituted to its original volume with distilled water.

EXAMPLE 2

Live canine corona virus vaccine-B

Live attenuated virus of the strain IN/SAV/Cl in a tissue culture fluid from canine A72 cells is mixed with the freeze-drying stabilizer according to Example 1, and 1 ml portions of this mixture each containing about $10^5$ pfu of the virus are filled into single dose vials which are subsequently sealed.

EXAMPLE 3

Inactivated canine corona virus vaccine

Tissue culture fluid from canine A72 cells infected with the virus IN/SAY/Cl (titer $10^8$ pfu/ml) is inactivated by the addition of β-propionic acid (final concentration 1:500). The pH is brought back to approximately a value of 7 by the addition of NaOH (0.1 mol/l).

This material is mixed with an adjuvant in the following proportions:

1 ml inactivated virus-infected tissue culture fluid 0.18 ml 2% aluminium phosphate solution 0.02 ml 1.2 mol/l glycine buffer of pH 9 130 µg Quil A.

This mixture is filled into a vial.

We claim:

1. An essentially pure culture of the canine corona virus strain deposited at the Collection Nationale de Cultures de Micro-organismes of Institut Pasteur, having the accession number I-743, or viruses derived by passaging said strain.

* * * * *